United States Patent
Yamazoe et al.

(10) Patent No.: US 10,444,146 B2
(45) Date of Patent: Oct. 15, 2019

(54) OPTICAL PROBE, LIGHT INTENSITY DETECTION, IMAGING METHOD AND SYSTEM

(71) Applicant: CANON U.S.A., INC., Melville, NY (US)

(72) Inventors: Kenji Yamazoe, Tochigi (JP); Seiji Takeuchi, Newton, MA (US)

(73) Assignee: CANON U.S.A., INC., Melville, NY (US)

( * ) Notice: Subject to any disclaimer, the term of this patent is extended or adjusted under 35 U.S.C. 154(b) by 0 days.

(21) Appl. No.: 16/062,397

(22) PCT Filed: Dec. 28, 2016

(86) PCT No.: PCT/US2016/068848
§ 371 (c)(1),
(2) Date: Jun. 14, 2018

(87) PCT Pub. No.: WO2017/117203
PCT Pub. Date: Jul. 6, 2017

(65) Prior Publication Data
US 2018/0372633 A1    Dec. 27, 2018

Related U.S. Application Data

(60) Provisional application No. 62/271,887, filed on Dec. 28, 2015.

(51) Int. Cl.
*A61B 1/00* (2006.01)
*G01N 21/47* (2006.01)
(Continued)

(52) U.S. Cl.
CPC ..... *G01N 21/4795* (2013.01); *A61B 1/00096* (2013.01); *A61B 1/00165* (2013.01);
(Continued)

(58) Field of Classification Search
CPC .... G01J 3/2823; A61B 5/0066; A61B 5/0084; A61B 5/0073; G01N 21/4795
See application file for complete search history.

(56) References Cited

U.S. PATENT DOCUMENTS

| 3,976,360 A | 8/1976 | Schroder |
| 4,074,306 A | 2/1978 | Kakinuma et al. |

(Continued)

FOREIGN PATENT DOCUMENTS

| WO | 2007/084903 A1 | 7/2007 |
| WO | 2014031748 A1 | 2/2014 |

(Continued)

OTHER PUBLICATIONS

Zeidan, A et al. "Miniature forward-viewing spectrally encoded endoscopic probe", Optics Letters, Aug. 15, 2014, pp. 4871-4874, vol. 39, Issue 16.

(Continued)

*Primary Examiner* — Jonathan M Hansen
(74) *Attorney, Agent, or Firm* — Canon U.S.A., Inc. I.P. Division

(57) ABSTRACT

The present invention relates generally to apparatus and methods for endoscopy which includes a probe, a first and a second optical fiber to guide light, a third optical fiber to capture light; and a switch configured to operate the first optical fiber and second optical fiber. Light dispersed by the first optical fiber at least partially overlaps light dispersed by the second optical.

19 Claims, 7 Drawing Sheets

(51) Int. Cl.
*A61B 5/00* (2006.01)
*G01N 21/27* (2006.01)
*G01N 33/483* (2006.01)
*A61B 1/04* (2006.01)
*A61B 1/055* (2006.01)
*A61B 1/06* (2006.01)
*A61B 1/07* (2006.01)

(52) U.S. Cl.
CPC .......... *A61B 1/00172* (2013.01); *A61B 1/042* (2013.01); *A61B 1/055* (2013.01); *A61B 1/0669* (2013.01); *A61B 1/07* (2013.01); *A61B 5/0066* (2013.01); *A61B 5/0073* (2013.01); *A61B 5/0084* (2013.01); *G01N 21/27* (2013.01); *G01N 33/4833* (2013.01)

(56) References Cited

U.S. PATENT DOCUMENTS

| | | |
|---|---|---|
| 4,264,127 A | 4/1981 | Schumacher et al. |
| 5,208,882 A | 5/1993 | Strasser et al. |
| 5,279,280 A | 1/1994 | Bacich et al. |
| 5,909,529 A | 6/1999 | Bhagavatula |
| 6,341,036 B1 | 1/2002 | Tearney et al. |
| 6,485,413 B1 | 11/2002 | Boppart et al. |
| 6,661,513 B1 | 12/2003 | Granger |
| 6,831,781 B2 | 12/2004 | Tearney et al. |
| 6,858,859 B2 | 2/2005 | Kusunose |
| 7,003,196 B2 | 2/2006 | Ghiron |
| 7,342,659 B2 | 3/2008 | Horn et al. |
| 7,448,995 B2 | 11/2008 | Wiklof et al. |
| 7,796,270 B2 | 9/2010 | Yelin et al. |
| 7,843,572 B2 | 11/2010 | Tearney et al. |
| 7,859,679 B2 | 12/2010 | Bouma et al. |
| 8,045,177 B2 | 10/2011 | Tearney et al. |
| 8,145,018 B2 | 3/2012 | Shishkov et al. |
| 8,203,708 B2 | 6/2012 | Lee et al. |
| 8,289,522 B2 | 10/2012 | Tearney et al. |
| 8,780,176 B2 | 7/2014 | Yelin |
| 8,804,133 B2 | 8/2014 | Yelin et al. |
| 8,812,087 B2 | 8/2014 | Yelin et al. |
| 8,818,149 B2 | 8/2014 | Shishkov et al. |
| 8,838,213 B2 | 9/2014 | Tearney et al. |
| 9,057,594 B2 | 6/2015 | Kang et al. |
| 9,254,089 B2 | 2/2016 | Tearney et al. |
| 9,295,391 B1 | 3/2016 | Tearney et al. |
| 2002/0114566 A1 | 8/2002 | Fairchild et al. |
| 2002/0145815 A1 | 10/2002 | Moriyama et al. |
| 2003/0027328 A1 | 2/2003 | Cunningham et al. |
| 2003/0142934 A1 | 7/2003 | Pan et al. |
| 2004/0147810 A1 | 7/2004 | Mizuno |
| 2004/0174529 A1 | 9/2004 | Maznev et al. |
| 2005/0078374 A1 | 4/2005 | Taira et al. |
| 2005/0155704 A1 | 7/2005 | Yokajty et al. |
| 2007/0188855 A1 | 8/2007 | Shishkov et al. |
| 2007/0233396 A1 | 10/2007 | Tearney et al. |
| 2007/0276187 A1 | 11/2007 | Wiklof et al. |
| 2008/0013960 A1 | 1/2008 | Tearney et al. |
| 2008/0097225 A1 | 4/2008 | Tearney et al. |
| 2009/0141360 A1 | 6/2009 | Koyama |
| 2009/0153932 A1 | 6/2009 | Davis et al. |
| 2010/0210937 A1 | 8/2010 | Tearney et al. |
| 2011/0237892 A1 | 9/2011 | Tearney et al. |
| 2011/0275899 A1 | 11/2011 | Tearney et al. |
| 2012/0112094 A1 | 5/2012 | Kao et al. |
| 2012/0212595 A1 | 8/2012 | Parmar et al. |
| 2013/0012771 A1 | 1/2013 | Robertson |
| 2013/0329224 A1* | 12/2013 | Takaoka ............ A61B 1/00096 356/402 |
| 2013/0331709 A1 | 12/2013 | Le et al. |
| 2014/0153864 A1 | 6/2014 | Sinclair et al. |
| 2014/0221747 A1 | 8/2014 | Tearney et al. |
| 2014/0285878 A1 | 9/2014 | Escuti et al. |
| 2014/0378846 A1 | 12/2014 | Hosoda et al. |
| 2015/0045622 A1 | 2/2015 | Shishkov et al. |
| 2015/0131098 A1 | 5/2015 | Yang et al. |
| 2015/0335248 A1 | 11/2015 | Huang et al. |
| 2016/0341951 A1* | 11/2016 | Tearney ............ A61B 1/00096 |
| 2017/0176736 A1 | 6/2017 | Yamamoto et al. |

FOREIGN PATENT DOCUMENTS

| | | |
|---|---|---|
| WO | 2014104405 A1 | 7/2014 |
| WO | 2015/042093 A1 | 3/2015 |
| WO | 2015/116951 A2 | 8/2015 |
| WO | 2015116939 A1 | 8/2015 |
| WO | 2015116974 A1 | 8/2015 |
| WO | 2017/024145 A1 | 2/2017 |
| WO | 2017/106347 A1 | 6/2017 |
| WO | 2017/139657 A1 | 8/2017 |
| WO | 2017/218496 A1 | 12/2017 |

OTHER PUBLICATIONS

Pitris, C. et al., ("A GRISM-based probe for spectrally encoded confocal microscopy" Optics Express, Jan. 27, 2003, pp. 120-124, vol. 11, No. 2.

Yelin, D., et al., "Three-dimensional miniature endoscopy", Nature, Oct. 19, 2006, p. 765, vol. 443.

Kang, D., et al., "Minature grating for spectrally-encoded endoscopy", Lab Chip, 2013, pp. 1810-1816, vol. 13, No. 9.

Kang, D., et al., "Spectrally-encoded color imaging", Optics Express, Aug. 17, 2009, pp. 15239-15247, vol. 17, No. 17.

Barlev, O., et al., "Design and experimental investigation of highly efficient resonance-domain diffraction gratings in the visible spectral region", Applied Optics, Dec. 1, 2012, pp. 8074-8080, vol. 51, No. 34.

Yun, et al., "High-speed spectral-domain optical coherence tomography at 1.3 μm wavelength", Opt Express, Dec. 29, 2003, pp. 3598-3604, No. 11, vol. 26.

Tearney, G.J., et al., "Spectrally encoded miniature endoscopy", Optics Letters, Mar. 15, 2002, pp. 412-414, vol. 27, No. 6.

Bai, B., et al. "Optimization of nonbinary slanted surface-relief gratings as high-efficiency broadband couplers for light guides", Applied Optics, Oct. 1, 2010, pp. 5454-5464, vol. 49, No. 28.

\* cited by examiner

OPTICAL PROBE, LIGHT INTENSITY DETECTION, IMAGING METHOD AND SYSTEM

CROSS-REFERENCE TO RELATED APPLICATION(S)

This application is a national stage application of PCT/US16/68848 filed Dec. 28, 2016 and claims priority to U.S. Provisional Application Ser. No. 62/271,887 filed 28 Dec. 2015, the content of each of which are incorporated herein by reference in their entirety.

FIELD OF THE DISCLOSURE

The present invention relates generally to apparatus and methods for endoscopy and, more particularly to spectrally encoded endoscopy probes for obtaining information having a wide field of view, methods for acquiring the image, and methods of making the endoscope.

BACKGROUND OF THE DISCLOSURE

Medical probes have the ability to provide images from inside the patient's body. Considering the potential harm capable to a human body caused by the insertion of a foreign object, it is preferable that the probe be as small as possible. Additionally, the ability to provide image within small pathways such as small vessels, ducts, needles, incisions, gaps, dictates the use of a small probe.

One particularly useful medical probe is the spectrally encoded endoscopy ("SEE"), which is a miniature endoscope that can conduct high-definition imaging through a sub-mm diameter probe. With SEE, broadband light is diffracted by a grating at the tip of the probe, producing a dispersed spectrum on the sample. Light returned from the sample is detected using a spectrometer; and each resolvable wavelength corresponds to reflectance from a different point on the sample. The principle of the SEE technique and SEE probe, having a diameter of 0.5 mm, i.e., 500 µm, has been reported by D. Yelin et al. [(Nature Vol. 443, 765-765 (2006)]. SEE can produce high-quality images in two- and three-dimensions.

One of the technical challenges for fabricating SEE probes has been to conduct wide field of view (FoV) SEE imaging (also called wide FoV SEE imaging). Until now, in order to increase the FoV, it was necessary to either use the light source having a broader spectral range (wavelength range or bandwidth), or to reduce the grating pitch to disperse the light to achieve greater diffraction angle. However, both methods have approached their physical or fabrication limits, resulting in a SEE probe capable of yielding a FoV of approximately 50°.

Accordingly, it is particularly beneficial to disclose a new SEE probe that has wider FoV, for example greater than 60°, and an apparatus to use such a probe, particularly for imaging in a small space.

SUMMARY

Thus, to address such exemplary needs, the presently disclosed apparatus, systems, and methods for miniature endoscopes having a wide FoV (more than 60°) are herein provided. According to the present subject matter, an exemplary embodiment of an apparatus and complimenting methods and systems can be provided for establishing SEE probes that have more than 60° FoV.

The present disclosure teaches an apparatus utilizing multiple illumination fibers and image processing to yield better images of a subject using a SEE probe. In addition, the subject SEE probe is designed such that the spectrally-encoded line from the two or more illumination fibers has overlap, as shown in FIG. 7, dramatically improving the FoV. The final image is given by logical disjunction of the image obtained from each spectrally-encoded line.

In one embodiment of the present disclosure, an apparatus for endoscopy is provided, having a probe, a first optical fiber to guide light, a second optical fiber to guide light, a third optical fiber to capture light, and a switch configured to operate the first optical fiber and second optical fiber, wherein light dispersed by the first optical fiber overlaps light dispersed by the second optical fiber.

In another embodiment, the subject apparatus may incorporate a spectrally dispersive component that receives light from the first optical fiber and disperses the light. In another embodiment, a spectrally dispersive component is utilized to disperse light received from the second optical fiber.

In yet another embodiment of the subject disclosure, light guided by the first optical fiber or second optical fiber is directed to a mirror prior to introduction to a spectrally dispersive component. In this embodiment, the angle of incident of light provided by the optical fiber is dramatically different than if the light was not reflected by the mirror.

In various embodiments of the subject disclosure, light provided by the first optical fiber overlaps light provided by the second optical fiber, either with or without the aid of the mirror, leading to a overlapped large field of view which may be stitched to produce a large image of the subject. For example, a larger image of an in vivo tissue may be produced and viewed.

In yet another embodiment of the subject disclosure, the first optical fiber and/or second optical fiber are configured to be offset from the optical axis of the probe.

In further exemplary embodiment of the subject disclosure, the third optical fiber may act as a detection fiber for collecting light reflected from the subject. The third optical fiber may be in communication with a spectrometer for reading the light spectrum to be sent to a processor which produces an image.

In various exemplary embodiments, a light source may be incorporated to provide light to the optical fibers. In additional embodiments, a mechanical scan unit, incorporating a rotational mechanism, and configured to rotate the probe in oscillatory motion or in continuous rotating motion, may be incorporated. In yet additional exemplary embodiments, a processing in communication with the apparatus, and configured to process information received from the apparatus, may be incorporated.

These and other objects, features, and advantages of the present disclosure will become apparent upon reading the following detailed description of exemplary embodiments of the present disclosure, when taken in conjunction with the appended drawings, and provided paragraphs.

BRIEF DESCRIPTION OF THE DRAWINGS

Further objects, features and advantages of the present invention will become apparent from the following detailed description when taken in conjunction with the accompanying figures showing illustrative embodiments of the present invention.

Figure 1:
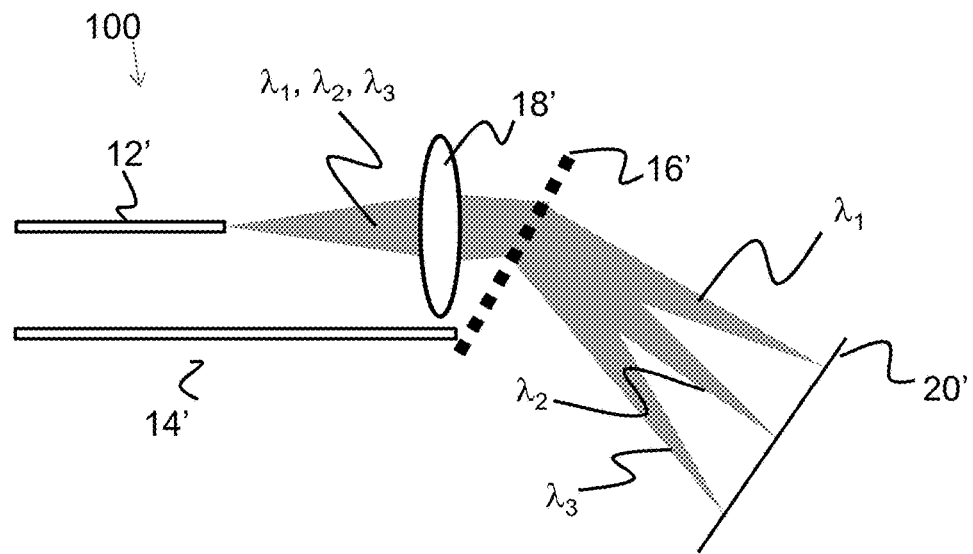
FIG. 1 depicts a SEE probe with accompanying components typical of the prior art.

Throughout the Figures, the same reference numerals and characters, unless otherwise stated, are used to denote like features, elements, components or portions of the illustrated embodiments. In addition, reference numeral(s) including by the designation "'" (e.g. 12' or 24') signify prior art elements and/or references. Moreover, while the subject invention will now be described in detail with reference to the Figures, it is done so in connection with the illustrative embodiments. It is intended that changes and modifications can be made to the described embodiments without departing from the true scope and spirit of the subject disclosure as defined by the appended paragraphs.

DETAILED DESCRIPTION OF THE DISCLOSURE

FIG. 1 depicts an exemplary SEE probe typical of the prior art. This prior art SEE probe 100 includes an illumination fiber 12', a focusing lens 18', and a diffraction grating 16'. Broadband light is relayed thought the illumination fiber 12' and focused by the lens 18'. In FIG. 1, the broadband light includes, for example three wavelengths: $\lambda_1$, $\lambda_2$, and $\lambda_3$ ($\lambda_1<\lambda_2<\lambda_3$). The light is then diffracted by the diffraction grating 16', and each wavelength is focused on a unique location on the subject 20' being imaged. Accordingly, the light can be focused into a line rather than a point. This line is termed as a spectrally-encoded line. Light reflected by the subject 20 is relayed back to a detection fiber 14' and is delivered to a spectrometer 24' in FIG. 2, which will be explained in the following paragraphs. At the spectrometer 24', the spectrum of the returning light is read, which renders a line image of the subject 20'.

Figure 2:
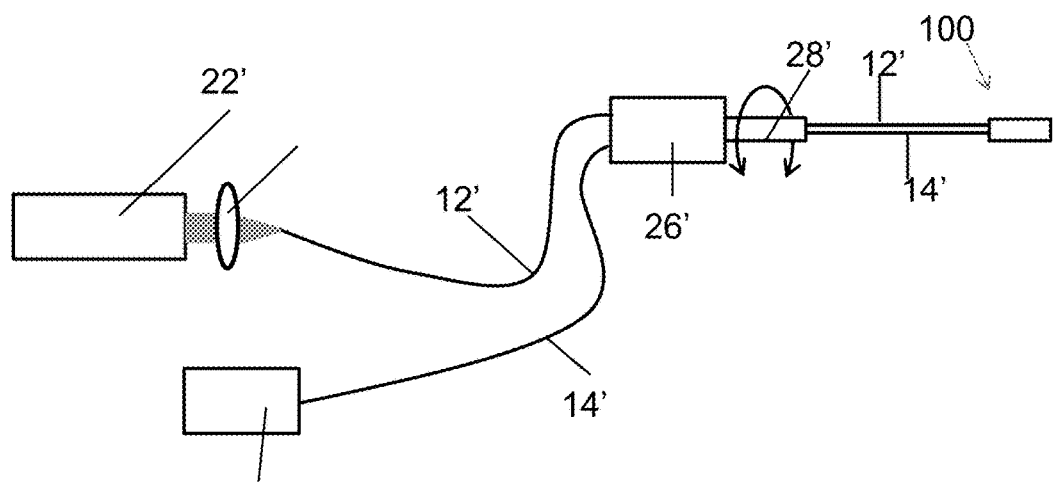
FIG. 2 provides a schematic diagram of an imaging system incorporating the SEE probe depicted in FIG. 1, typical of the prior art.

Details of the prior art SEE system described herein, which acquires the image from the SEE probe is provided in FIG. 2. In FIG. 2, the light source 22' outputs broadband light, which is coupled into an illumination fiber 12'. The illumination fiber 12' is connected through a junction unit 26' to the illumination fiber 12' that is attached to the SEE probe 10. The light scattered back from the subject 20' is collected by a detection fiber 14', which is relayed through the junction unit 26' to a detector 24' in which the intensity of selected wavelength is detected. An example of a detector may be a spectrometer.

The SEE probe 10' can be scanned rotationally along the optical axis of the lens by a mechanical scan unit 28' to obtain the two-dimensional image of the object. The mechanical scan 28' is typically done by Galvo scanner or motor. By scanning the spectrally-encoded line back and forth by half angle of α, the FoV in one direction is approximately 2α. The FoV of spectrally-encoded line is determined by the dispersion angle of the minimum wavelength and the maximum wavelength. In FIG. 1, the FoV is determined by the dispersion angle of $\lambda_1$ and $\lambda_3$. If we increase the rotation angle, we can increase the FoV in one direction. Using a galvanometric motor, the practical limit of the rotation would be approximately α=35°. It would be very hard to take an image at α>35°. If the pitch of the grating is 450 nm and broadband light from 450 nm to 750 nm is used, the FoV of spectrally-encoded line is limited to approximately 45°.

To increase the FoV of the spectrally-encoded line, we need to increase the spectrum range, which is limited by the visible wavelength range, if we restrict to visible light imaging. Therefore, in order to further increase the field of view, it is necessary to increase the diffraction angle. For this purpose, the simplest method is to reduce the grating pitch, but fabrication of a grating with less than 450 nm pitch is very difficult and costly to accomplish. In addition, the diffraction efficiency decreases as the grating pitch is decreased. Therefore, to increase the FoV of spectrally-encoded line, it is necessary to reinvent the fundamental methodology relating to SEE probes.

Figure 3:
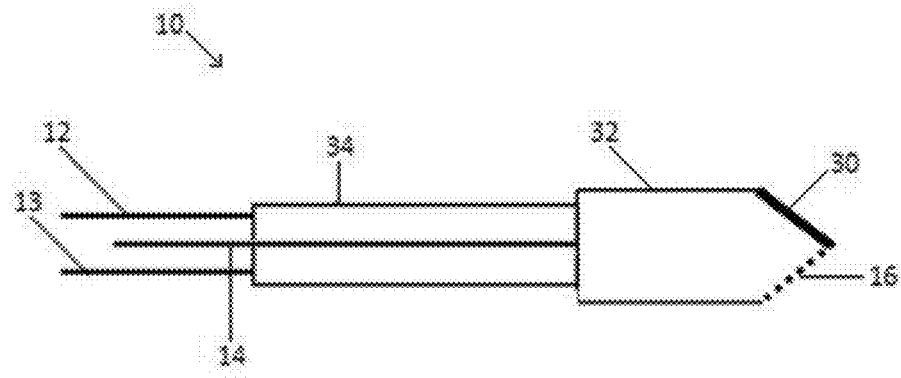
FIG. 3 provides a schematic diagram of a wide FoV SEE probe, in accordance with one or more embodiments of the present subject matter.
Figure 4:
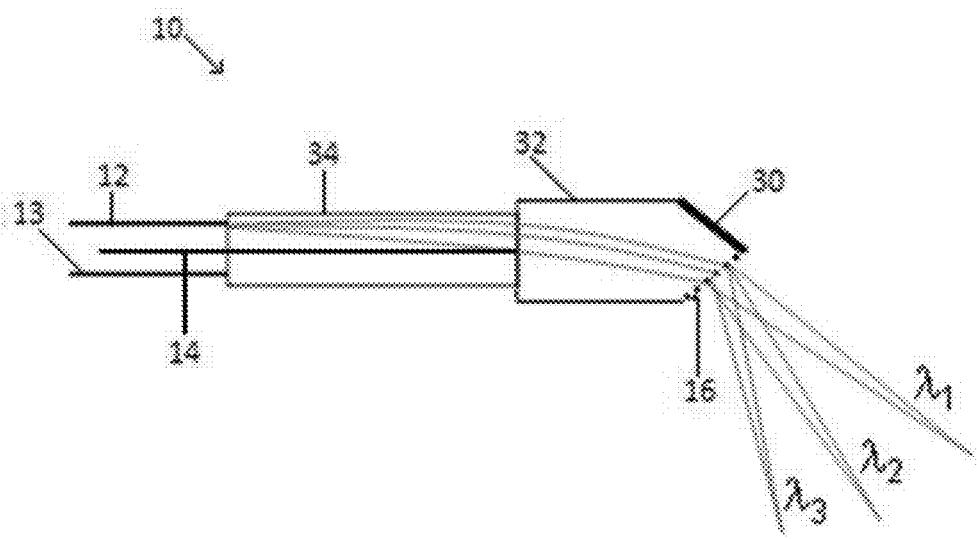
FIG. 4 depicts a schematic diagram of a wide FoV SEE probe, detailing the path of light from an illumination fiber, according to one or more embodiments of the present subject matter.
Figure 5:
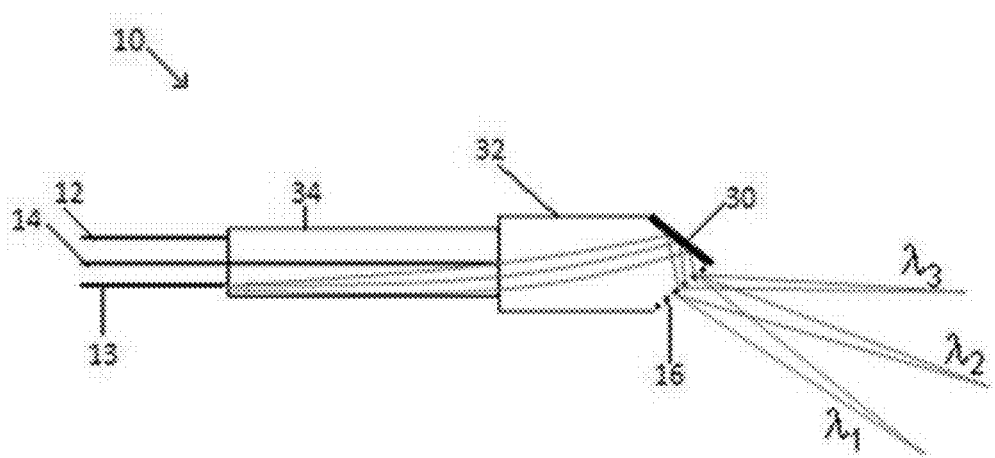
FIG. 5 depicts a schematic diagram of a wide FoV SEE probe, detailing the path of light from an illumination fiber, according to one or more embodiments of the present subject matter.

FIG. 3 provides a schematic diagram of a wide FoV SEE probe 10, in accordance with one or more embodiments of the present subject matter. As depicted in FIG. 3, a gradient index (GRIN) lens 34 is used as the focusing lens. A transparent rod 32 with a wedge-polished end is attached to the GRIN lens 34. The wedge-polished end has a polished surface 30 and a diffraction grating 16. In this design, two illumination fibers 12 and 13 are attached to the GRIN lens 34. The first illumination fibers 12 and second illumination fiber 13, are offset perpendicular to the center-line of the transparent rod 32. A broadband light including, for example, wavelengths: $\lambda_1$, $\lambda_2$, and $\lambda_3$ ($\lambda_1<\lambda_2<\lambda_3$) from the first illumination fiber 12 is directly incident on the grating 16 and then is diffracted as shown in FIG. 4. A broadband light including, for example, wavelengths: $\lambda_1$, $\lambda_2$, and $\lambda_3$ ($\lambda_1<\lambda_2<\lambda_3$) from the second illumination fiber 13 is first directly incident on the polished surface 16 to be reflected and then diffracted as shown in FIG. 5. Due to this reflected arrangement, the shorter wavelength a, of the first illumination fiber 12 is diffracted closer to the optical axis, whereas the longer wavelength $\lambda_3$ of the second illumination fiber 13 is diffracted closer to the optical axis. These two diffractions allow for a wider range diffraction angle, which results in the dramatically increased FoV of the subject matter SEE Probe 10.

More specific examples will be explained in the following embodiments. Although the embodiments are provided herein, they are no way restrictive of the full scope of the present subject matter, and act only as examples of the disclosed technology.

Embodiment 1: Wide Field of View

Figure 6:
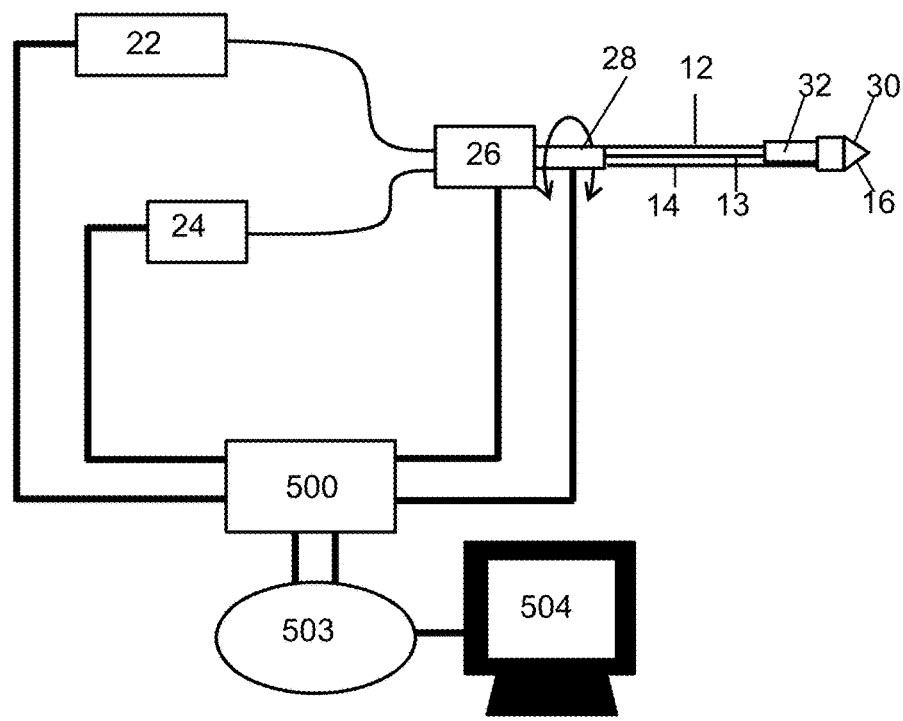
FIG. 6 illustrates a schematic diagram of SEE imaging system explained in Embodiments 1 and 2, according to one or more embodiments of the present subject matter.

In this Embodiment, the wide FoV SEE probe 10 system is explained in conjunction with FIG. 6. The parameters of the wide FoV probe will be provided as well. First, the wide FoV SEE probe 10 is attached to the junction unit 26. The junction unit 26 and the mechanical scan unit 28 is in a handpiece. However, the vibration from the mechanical scan unit 28 in the handpiece may affect the precise user handling of the probe. Thus, the mechanical scan unit 28 can be outside of the handpiece to reduce the vibration to the handpiece.

The broadband light with the wavelength of 450-750 nm is radiated from the light source 22, which is controlled by a computer system 500 (detailed below). For this embodiment, the maximum wavelength $\lambda_{max}$ is 750 nm and the minimum wavelength $\lambda_{min}$ is 450 nm. A single-mode fiber is used to guide the broadband light to the junction unit 26. Inside the junction unit 26, there is a switching device controlled by the computer system 500. The switching device can switch the fiber to couple the light according to the command from the computer system 500.

The wide FoV SEE probe 10 of the same type as shown in FIG. 3 is implemented. The GRIN lens 34 (central refractive index=1.61; refractive index distribution constant=0.42; length=3.8 mm; diameter=0.35 mm) is used as the focusing lens. An optical rod 32 with a wedge-polished end is attached 10 the GRIN lens 34. The length without the wedge is 2.5 m. The lower wedge surface has a grating 16 with a period of 450 nm, which is stumped onto an epoxy on the optical rod 32. The grating angle from the optical axis is nearly 40°. The upper wedge surface is mirror polished to function as a mirror 30. The polished surface angle is nearly 40° from the optical axis. Two single-mode illumination fibers 12 and 13 are attached to the GRIN lens 34 with symmetrical 0.11 mm offset perpendicular to the wedge intersection line. The detection fiber 14 is attached to the GRIN lens 34. The wide FoV SEE probe 10 is connected to the mechanical scan unit 28, which in turn is connected to the junction unit 26.

In preparation, light from the light source 22 is coupled into either the first illumination fiber 12 or the second illumination fiber 13, wherein the spectrally-encoded line may be formed through the grating 16, onto the subject 20. The reflected light from the subject 20 is detected by the detection fiber 14, which usually is a multi-mode fiber to collect more light than a single-mode fiber. The detection fiber 14 guides the reflected light to the spectrometer 24 through the junction unit 26. The spectrometer 24 reads out the spectrum of the returning light, which is sent to the computer system 500 for data processing. The computer system 500 processes each line image to display an image to the monitor 504. A user, for example a doctor, can operate the computer system 500 through a given user interface 503.

Figure 9:
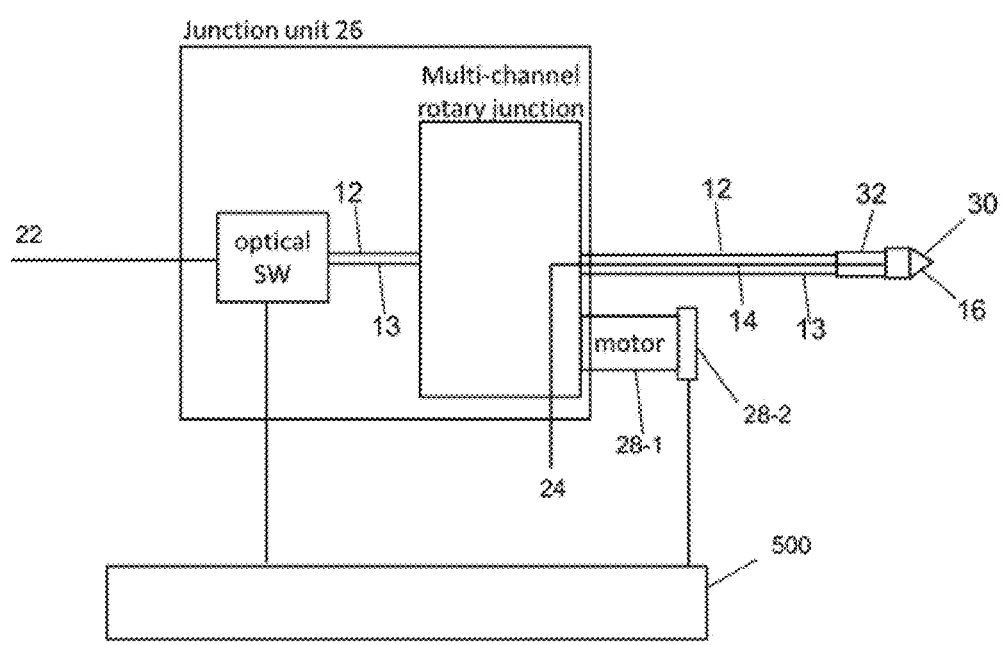
FIG. 9 depicts a detailed block diagram of an imaging method provided in the present disclosure, according to one or more embodiments of the present subject matter.

FIG. 9 depicts a detailed block diagram of an imaging method provided in the present disclosure, according to one or more embodiments of the subject disclosure. In FIG. 9, the junction unit 26 includes an optical switch and a multi-channel rotary junction. The scan unit 28 includes a motor body 28-1 and a motor control unit 28-2. The control unit 28-2 include at least a substrate for the motor control. The control unit 28-2 also may include an encoder scale jointed to the end of the motor shaft and a sensor. The encoder scale rotates similarly to the motor shaft. The sensor detects the rotation of the encoder scale and outputs the rotating angle information (position information). The computer system 500 inputs the signal indicating the angle position (position information) output by the sensor (the control unit 28-2) and controls the optical switch according to the input signal from the control unit 28-2. In one exemplary embodiment, a stepping Galvo motor may be implemented as a motor body 28-1, whereby the encoder scale and a sensor could be omitted.

With regards to the multi-channel rotary joint/junction mentioned in the present disclosure, Applicant incorporates by reference various well-known rotary joint/junctions, known to those of ordinary skill in the art, including, but not limited to, U.S. Patent Publication No. 2010/0195956 to Zhang, et al., and U.S. Pat. No. 4,842,355 to Gold, et al.

Exemplary Method for Obtaining an Image.

The computer system 500 is initiated and sends a command to the switching device situated in the junction unit 26, to couple broadband light to first illumination fiber 12. Then, the computer system 500 sends a command to mechanical scan unit 28 to rotate the wide FoV probe 10 for one time by an angle of $-\alpha$ to $+\alpha$ or vise versa. The spectrally-encoded line is scanned at the predetermined rotation step of $\Delta\alpha$. For example, to image 1000 pixels in rotating direction, $\Delta\alpha=2\alpha/1000$. The mechanical scan unit 28 continuously moves the probe 10. During the continuous moving, the line image is obtained at the sampling rotation rate of $\Delta\alpha$. Let $\lambda_{min}$ be the diffraction angle of the maximum wavelengths $\lambda_{max}$. Also, let $\lambda_{max}$ be the diffraction angle of the minimum wavelengths $\lambda_{min}$. The spectrally-encoded line by the diffraction angle between $\lambda_{min}$ and $\lambda_{max}$ is obtained. The image is obtained according to these diffraction angles. This two-dimensional ("2-D") image is termed as Image 1.

Thereafter, the computer system 500 sends a command to the switching device to couple the light to the second illumination fiber 13. The computer system 500, then, sends a command to the mechanical scan unit 28 to rotate the wide FoV probe 10 by $-\alpha$ to $+\alpha$ or vice cersa. Let $)_{min}$ and $\psi_{max}$ be the diffraction angles of $\lambda_{min}$ and $\lambda_{max}$, respectively. The image is obtained from the spectrally-encoded line whose diffraction angle is limited between $\psi_{min}$ and $\psi_{max}$. This 2-D image is termed as Image 2.

Figure 7:
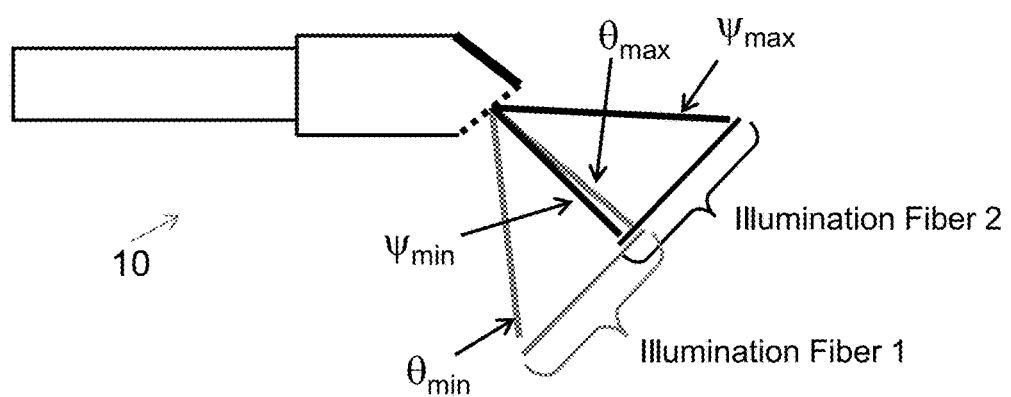
FIG. 7 illustrates an exemplary method of how the wide FoV SEE probe is realized, or how the switchable viewing direction SEE probe is realized, according to one or more embodiments of the present subject matter.

In this step, Image 1 and Image 2 are combined by the computer system 500 to obtain a wide FoV image. As schematically illustrated in FIG. 7, the FoV is clearly increased to a range from $\lambda_{min}$ to $\psi_{max}$ with the subject matter presented here. Repeating these steps would provide a video image of the subject. In this Embodiment, the FoV in the spectrally-encoded direction is increased to more than 80°.

Exemplary Flow of the Subject Disclosure.

Until now, the structure of the wide FoV probe 10, imaging method, and imaging system with the wide FoV probe 10 has been described. Below, and in conjunction with FIG. 10, an exemplary procedure of the image acquisition process is explained in detail. As this process is exemplary, it is contemplated that various additional steps, substitute steps, omission of steps, derivative steps, and combinations of the aforementioned, are contemplated and considered to be encompassed by the present subject matter.

Figure 10:
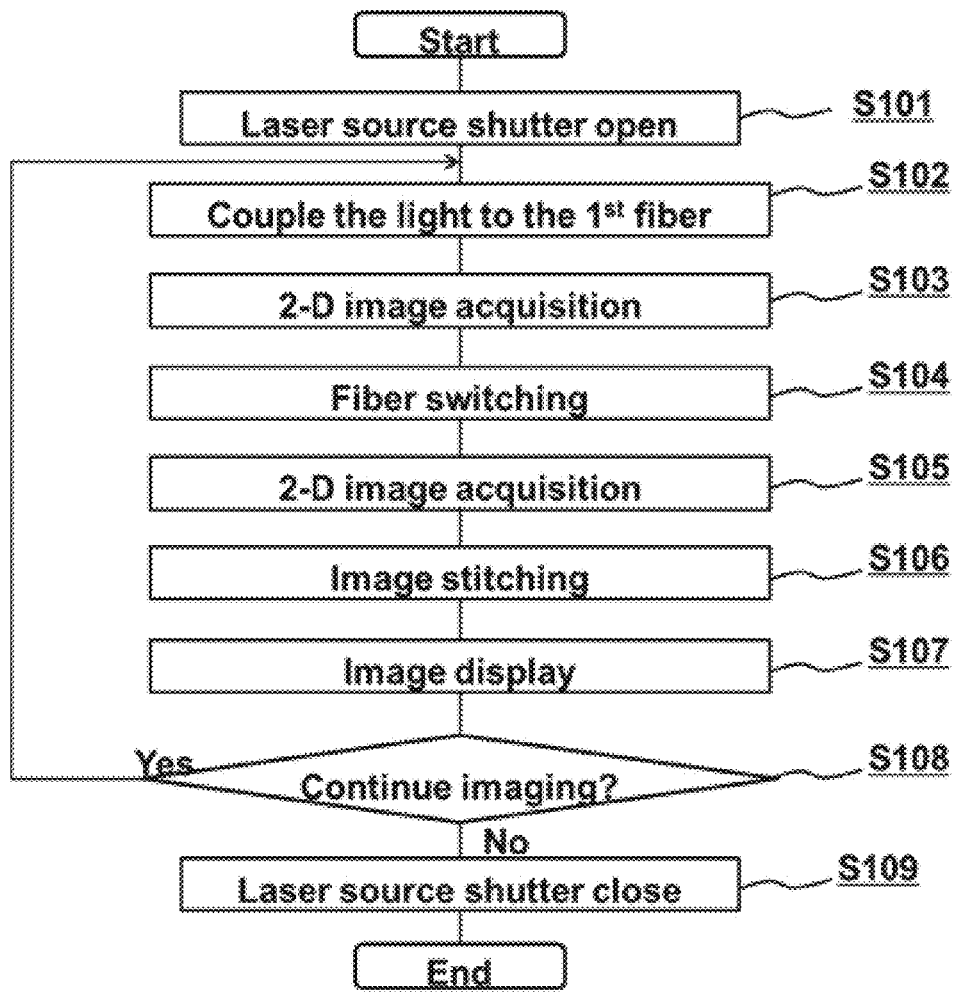
FIG. 10 provides an exemplary flow chart detailing the procedure of the image acquisition process, according to one or more embodiments of the present subject matter.

The flowchart of the image acquisition process with the wide FoV probe 10 presented in FIG. 10, incorporates a user of this device to turn on the computer 500, monitor 504, and the laser source 22 for operation. The user then attaches the wide FoV probe 10 to the junction unit 26, to commence imaging.

In step S101, the shutter of the laser source 22 is opened by a command from the computer 500. The shutter can be mechanical or be controlled by software. When the shutter is open, light from the laser source 22 goes through the single mode fiber to the junction unit 26. In step S102, the light from the laser source 22 is coupled to the first illumination fiber 12 by a switching device inside the junction unit 26. The light reaches the tip of the wide FoV probe 10 followed by dispersion of the light by the grating 16 to illuminate the subject 20.

In step S103, an image is obtained by the light from the first illumination fiber 12. This step consists of collecting many line images, one of which is taken as follows. The dispersed light illuminates the subject 20 and a part of the light is reflected back from the subject 20 to return into the detection fiber 14. The detection fiber 14 guides the light to the spectrometer 24. The spectrum distribution is sent to the computer 500, which is converted into a line image of the subject 20. The computer 500 controls the rotation of the wide FoV probe 10 around the optical axis by sending a command to the mechanical scan unit 28. A back and forth rotation is conducted between $-\alpha$ and $+\alpha$, so that the angle of rotation of the wide PoV probe 10 is $2\alpha$. This back and forth rotation can be done, for example, by a Galvo motor. The computer 50o acquires the line image at a rotation angle of $\alpha_i$ ($1 \le i \le N$), where N is the number of the pixel in rotating direction. The simplest way of setting the rotation angle is for $\alpha_{j+1}-\alpha_j$ ($1 \le j < N$) to be constant. Another possible way of setting the rotation angle is for $|\tan(\alpha_{j+1})-\tan(\alpha_j)|(1 \le j < N)$ to be constant. When N line images are obtained, they are combined together to form a 2-D image.

In step S104, the fiber to illuminate the subject 20 is switched, i.e., the light from the laser source 22 is guided to the second illumination fiber 13 instead of the first fiber 12. This operation is conducted by a command from the computer 500.

Figure 11:
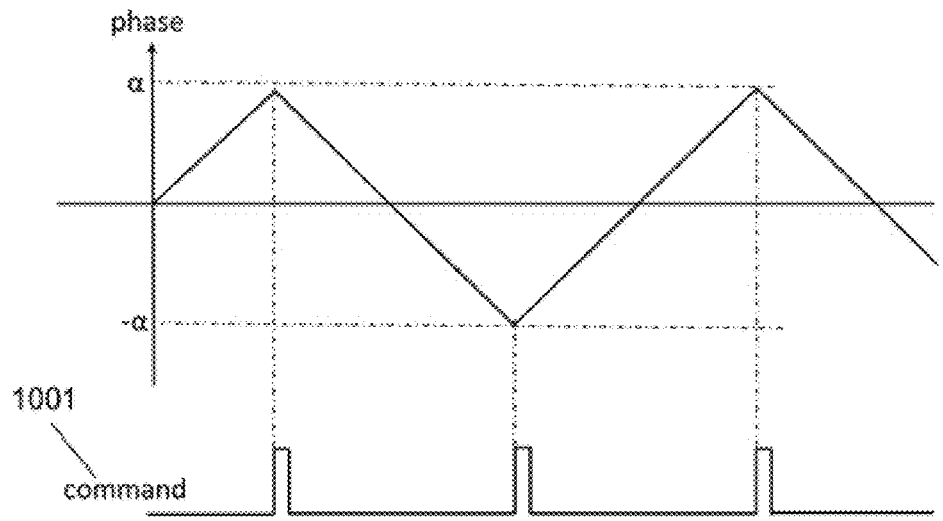
FIG. 11 illustrates an exemplary time chart for switching of the two illumination fibers 12 and 13 to achieve the wide FOV, according to one or more embodiments of the present subject matter.

FIG. 11 is provided to illustrate an exemplary time chart for switching between the two illumination fibers 12 and 13 to achieve the wide FoV. The computer system 500 inputs the rotation angle information to the motor, and determined if the input angle information corresponds to "$\alpha$" or "$-\alpha$". Based on the results, a switching signal is outputted (command 1001) to the optical switch in the junction unit 26 to change the rotation direction so that the wide FoV probe 10 rotates in the desired direction. The computer system 500 may determine the rotation angle at which the computer 500 acquires the line image, based on the rotation angle information provided by the sensor (control unit 28-2). The computer 500 may determine the rotation angle at which the computer 500 acquires the lime image based on the elapsed time from the computer system 500 input information output from the sensor. In addition, the computer system 500 may determines the rotation angle at which the computer 50o acquires the line image by the elapsed time from the timing in which the computer system outputs the command.

In further view of FIG. 10, in step S105, a 2-D image is acquired using the second illumination fiber. Since the process is the same as that of step S103, the details are omitted herein, and may be reference above.

In step S106, two 2-D images obtained in step S103 and S106 are combined together, which is often referred to as "image stitching". The two images have some overlap and the computer 500 determines which portions of the images are overlapped. Then, the computer 500 combines the two images according to the overlapped portions detected. The image stitching is not a special technique and can nowadays be found in commercial cameras. Therefore, detail of image stitching are incorporated by reference herein.

In step S107, the image combined in step S106 is displayed on the display 504. In step S108, if the computer 500 does not receive a quit command from the user, then the procedure may continue by returning to step S102; otherwise, it may go to step S109.

In step S109, to finish the operation safely, the computer 500 closes the shutter of the laser source 22. To shut down the whole system, the user may turn off the computer 500, laser source 22, and display 504.

The above explanation of the flowchart assumed using a Galvo motor to rotate the wide FoV probe 10 back and forth. However, in an alternative embodiment, it is possible to incorporate a standard rotation motor that continuously rotates in one direction. If a standard motor is utilized, steps S103 and S105 may be changed accordingly.

In step S103 or S105, a 2-D image is obtained by combining many line images. The dispersed light from either the illumination fiber 12 or 13 illuminates the subject 20 and the spectrum of the reflected light is analyzed via the detection fiber 14 by the spectrometer 24. The spectrum distribution output from the spectrometer 24 is converted into a line image of the subject 20. The motor embedded in the mechanical scan unit 28 continuously rotates the wide FoV probe 10 during image acquisition process. However, the line image is captured only at a predetermined rotation angle range between $-\alpha$ and $+\alpha$. In other words, if the rotation angle is not within from $-\alpha$ and $+\alpha$, no line image is captured. The computer 500 acquires the line image at a rotation angle of $\alpha_i$ ($1 \le i \le N$), where N is the number of the pixel in rotating direction. Apparently, $-\alpha \le \alpha_i \le +\alpha$. The simplest way of setting the rotation angle is for $\alpha_{j+1}-\alpha_j$ ($1 \le j < N$) to be constant. Another possible way of setting the rotation angle is for $|\tan(\alpha_{j+1})-\tan(\alpha_j)|(1 \le j < N)$ to be constant. When N line images are obtained, they are arranged together to form a 2-D image.

If the diffracted light from one of the illumination fibers goes forward along the optical axis, it is a good option to set $\alpha=180$ degree. By setting $\alpha=180$ degree, we can observe ahead of the wide FoV probe 10 to realize a forward viewing wide FoV SEE probe 10.

Embodiment 2: View Switching

In this Embodiment, a direction switchable SEE probe is disclosed. The SEE probe used in this Embodiment is similar to the probe disclosed in Embodiment 1, however the operation in obtaining images of the subject differs.

A user selects a viewing direction from either forward-view like direction or side-view like direction. If the use selects the forward-view like direction at the user interface unit 503, the computer system 500 sends a command to the optical switch inside the junction unit 26 to couple the light to the first illumination fiber 12. Under this condition the, previously disclosed, standard SEE image acquisition procedure, similar to step S103 in FIG. 10, is performed. The video image is then displayed in the monitor 504.

If the user prefers to switch the viewing direction, the user can select the side-view orientation via the user interface unit 503. In this instance, the computer system 500 sends a command to the optical switch to couple the light to the second illumination fiber 13. Under this condition the resultant image is obtained by the procedure similar to step S105 in FIG. 10. In this Embodiment, the image capturing process is the standard SEE image capturing process. However, the wide FoV probe 10 shown in FIG. 3 together with switching of the first and second illumination fibers, results in a direction switchable SEE probe.

Fabrication.

Fabrication of the wide FoV probe 10 and the imaging system is disclosed herein. The illumination fibers 12 and 13 may be fusion spliced into the GRIN lens 34. If the melting temperatures of the GRIN lens 34 and the illumination fibers 12 and 13 vary greatly, epoxy may be used in lieu of splicing to attach illumination fibers 12 and 13. As high intensity light may damage the epoxy between the illumination fibers and GRIN lens 34, we may fusion splice a coreless fiber (less than 1 mm length) to the illumination fibers. In this case, the coreless fiber is attached to the GRIN lens with epoxy.

The polished end surface of the GRIN lens 34 should be polished very smoothly. Usually, 0.3 µm polishing paper is good to finish the polishing. For the transparent rod 32, we can splice a glass rod to the GRIN lens 34, or glass rod can be attached to the GRIN lens 34 with epoxy. The transparent rod 32 may comprise of epoxy as well.

The grating 16 can be stamped on to the polished surface. An epoxy can be used for stamping. Alternatively or additionally, a grating sheet may be placed on the surface as well. Alternatively, injection molding may be utilized for one or both the polished surface and grating.

The detection fiber 14 should be attached to the side of the GRIN lens (as close as the plane formed by the optical axis and wedge intersection line). Its end surface should be cleaved or polished, and attached to the transparent rod 32. To reinforce the wide FoV probe 10, heat shrinking tube may be utilized around every component including the fibers. Currently, a heat shrinking tube with less than 5 µm wall thickness is available. Even if this heat shrinking tube is wrapped to the wide FoV probe 10, the wide FoV probe 10 diameter changes by less than 10 µm. Thus, the wide FoV probe 10 remains miniscule.

Figure 8:
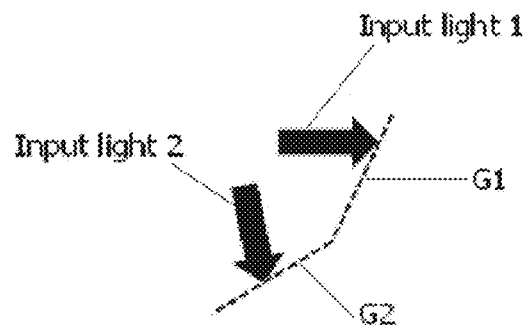
FIG. 8 provides a schematic diagram of a portion of an exemplary wide FoV SEE probe incorporating two gratings, according to one or more embodiments of the present subject matter.

Although the exemplary embodiments of the disclosure are described utilizing visible light, it is understood that invisible light may and can be incorporated or substituted into the wide FoV probe 10. The wide FoV probe 10 is not limited similar to the schematic diagrams presented in this disclosure. For example, we may use three or more illumination fibers. Or we may use two or more gratings. By way of example, FIG. 8 illustrates the use of two gratings G1 and G2, which may incorporate the use of one or more illumination fibers to capture an image of the subject. In this embodiment, it is possible to design a system wherein the diffracted light from the first grating G1 illuminated by the first illumination fiber 12 has a little overlap with the diffracted light from the first grating G2 illuminated by the second illumination fiber 2.

The mechanical scan unit 28 was configured to oscillate back and forth. In addition, the mechanical scan unit 28 may be configured to rotate. In this instance, a rotary junction may be incorporated to rotate at the junction unit 26. During the continuous rotation, the spectrally-encoded line is scanned only if the rotation angle is within a predetermined rotation angle range.

Furthermore, exemplary embodiments of the disclosure are provided with GRIN lenses 34, however other focusing component such as micro lens or ball lens can be incorporated and/or supplemented. Here we briefly comment on a GRIN lens 34 wherein rays approximately follow sinusoidal paths. A pitch of GRIN lens 34 is determined such that a light ray that has propagated one pitch has propagated one cycle of the sinusoidal path trajectory. Therefore, GRIN lenses 34 with lengths of one pitch and two-pitch have the identical optical property. Let $G_p$ be one pitch of a GRIN lens 34. No matter how many times we designed the wide FoV probe 10 with the GRIN lens 34, the length of the GRIN lens 34 was more than $(k+¼)G_p+0.1G_p$ and less than $(k+¼)G_p+0.3G_p$, where k is zero or a positive integer. This result gives us a framework of the wide FoV probe 10 design.

To protect the wide FoV probe 10, the wide FoV probe 10 can be in a tube with a window. Hypotube can be used for such a purpose. The detection fiber 14 and the wide FoV probe 10 are in a unit in the above embodiments, but they can be separated. For example, the detection fiber 14 can be a part of the protection tube. In this case, the mechanical scan unit 28 does not necessarily rotate the detection fiber 14, and the required power to the mechanical scan unit 28 can be reduced.

The exemplary procedures provided herein may be executed on and/or assisted by, or under the control of a computer system, executing one or more executable instructions stored on a computer-accessible medium. For example, when the computer system accesses the computer-accessible medium, it retrieves executable instructions therefrom and then executes the executable instructions. In addition or alternatively, a software arrangement can be provided separately from the computer-accessible medium, which can provide the instructions to the computer system so as to configure the processing arrangement to execute the above-described procedures.

Figure 12:
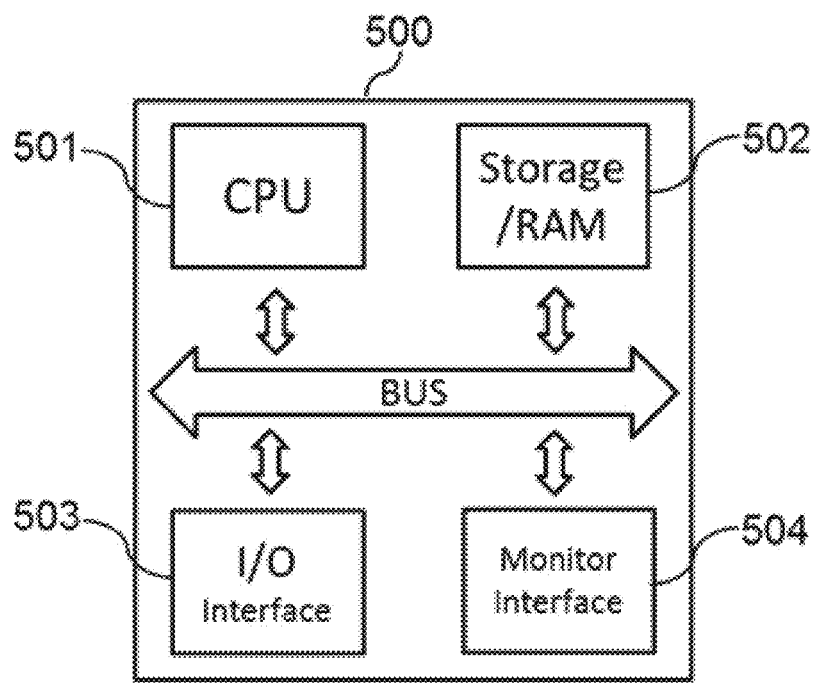
FIG. 12 illustrates a schematic diagram of an exemplary computer system to be incorporated with the SEE imaging system, according to one or more embodiments of the present subject matter.

Various components of the computer system 500 are provided in FIGS. 6 and 12. A computer system 500 may include a CPU 501, a Storage/RAM 502, an I/O Interface 503 and a Monitor interface 504. In addition, the computer system 500 may comprises one or more devices. For example, the one computer may include components 501, 502 and 503 and other computer may include component 504.

The CPU 501 is configured to read and perform computer-executable instructions stored in the Storage/RAM 502. The computer-executable instructions may include those for the performance of the methods and/or calculations described herein.

Storage/RAM 502 includes one or more computer readable and/or writable media, and may include, for example, a magnetic disc (e.g., a hard disk), an optical disc (e.g., a DVD, a Blu-ray), a magneto-optical disk, semiconductor memory (e.g., a non-volatile memory card, flash memory, a solid state drive, SRAM, DRAM), an EPROM, an EEPROM, etc. Storage/RAM 502 may store computer-readable data and/or computer-executable instructions. Each of components in the computer system 500 communicates each other via a bus. For example, the spectrum data from the spectrometer D is stored in the Storage/RAM 502 before the images captured in response to the illumination, reflection and detection of the subject, from illumination fibers 12 and 13, are stitched by the CPU 501.

The I/O interface 503 provides communication interfaces to input and output devices, which may include the light source 22, the spectrometer 24, the junction unit 26, the scan unit 28, the user interface unit 503, a microphone and a communication cable and a network (either wired or wireless). The user interface unit 503 may include a keyboard, a mouse, a touch screen, a light pen, a microphone and so on. The Monitor interface 504 provides communication interfaces to the Monitor.

The invention claimed is:

1. A apparatus for endoscopy comprising:
a probe;
a first optical fiber to guide light;
a second optical fiber to guide light;
a third optical fiber to capture light;
a switch configured to operate the first optical fiber and second optical fiber;
a mirror configured to reflect light from the second optical fiber; and
a spectrally dispersive component that receives light from the first optical fiber and the second optical fiber,
wherein light from the first optical fiber and dispersed by the spectrally dispersive component at least partially overlaps light from the second optical fiber and dispersed by spectrally dispersive component on a subject.

2. The apparatus according to claim 1, further comprising:
a processor configured to receive light detected by the third optical fiber,
wherein the light detected from the first optical fiber and the light captured by the second optical fiber may be stitched by the processor to compose a larger field of view.

3. The apparatus according to claim 1,
wherein the first optical fiber and second optical fiber are offset from the optical axis of the probe.

4. The apparatus according to claim 1,
wherein the third optical fiber is a detection fiber for detecting light reflected by a subject, wherein the reflected light is sourced from the first optical fiber and second optical fiber.

5. The apparatus according to claim 1, further comprising:
a light source for illuminating the first optical fiber and second optical fiber.

6. The apparatus according to claim 1, further comprising:
a spectrometer in communication with the third optical fiber, and configured to read light collected by the third optical fiber.

7. The apparatus according to claim 1, further comprising:
a mechanical scan unit, incorporating a rotational mechanism, and configured to rotate the probe in oscillatory motion or in continuous rotating motion.

8. The apparatus according to claim 1, further comprising:
a processor in communication with the apparatus, and configured to process information received from the apparatus to create an image.

9. An endoscopic system comprising:
a probe;
a first optical fiber to guide light;
a second optical fiber to guide light;
a third optical fiber to capture light;
a switch configured to operate the first optical fiber and second optical fiber,
a mirror configured to reflect light from the second optical fiber;
a spectrally dispersive component that receives light from the first optical fiber and the second optical fiber,
wherein light from the first optical fiber and dispersed by the spectrally dispersive component at least partially overlaps light from the second optical fiber and dispersed by spectrally dispersive component on a subject;
one or more light sources for illuminating the first optical fiber and second optical fiber;
a spectrometer in communication with the third optical fiber; and
a detector in communication with the spectrometer.

10. The endoscopic system according to claim 9, further comprising:
a mechanical scan unit, incorporating a rotational mechanism, and configured to rotate the probe in oscillatory motion or in continuous rotating motion.

11. An imaging method comprising the steps:
coupling a light into a first optical fiber;
acquiring a first image of a first portion of a subject;
switching the light from the first optical fiber to a second optical fiber;
acquiring a second image of a second portion of the subject by reflecting the light off a mirror,
wherein a spectrally dispersive component receives and disperses light from the first optical fiber and the second optical fiber,
wherein the second portion of the subject reflected from the mirror at least partially overlaps the first portion of the subject;
stitching the first image to the second image to form a combined image; and
displaying the combined image.

12. A apparatus for endoscopy comprising:
a probe;
a first optical fiber to guide light;
a second optical fiber to guide light;
a third optical fiber to capture light;
a switch configured to operate the first optical fiber and second optical fiber; and
a spectrally dispersive component that receives and disperses light from the first optical fiber,
wherein light dispersed by the first optical fiber at least partially overlaps light guided by the second optical fiber on a subject.

13. The apparatus according to claim 12, further comprising:
a spectrally dispersive component that receives light from the second optical fiber.

14. The apparatus according to claim 12, further comprising:
a processor configured to receive light detected by the third optical fiber,
wherein the light detected from the first optical fiber and the light captured from the second optical fiber may be stitched by the processor to compose a larger field of view.

15. The apparatus according to claim 12,
wherein the first optical fiber and second optical fiber are offset from the optical axis of the probe.

16. The apparatus according to claim 12,
wherein the third optical fiber is a detection fiber for detecting light reflected by a subject, wherein the reflected light is sourced from the first optical fiber and second optical fiber.

17. The apparatus according to claim 12, further comprising:
a light source for illuminating the first optical fiber and second optical fiber.

18. The apparatus according to claim 12, further comprising:
a spectrometer in communication with the third optical fiber, and configured to read light collected by the third optical fiber.

19. The apparatus according to claim 12, further comprising:
a mechanical scan unit, incorporating a rotational mechanism, and configured to rotate the probe in oscillatory motion or in continuous rotating motion.

* * * * *